United States Patent
Van Wyk

(10) Patent No.: US 9,696,126 B2
(45) Date of Patent: Jul. 4, 2017

(54) DETONATOR SYSTEM CONFIRMATION

(71) Applicant: DETNET SOUTH AFRICA (PTY) LTD, Woodmead (ZA)

(72) Inventor: Riaan Lingenfelder Van Wyk, Edenvale (ZA)

(73) Assignee: DETNET SOUTH AFRICA (PTY) LTD, Woodmead (ZA)

( * ) Notice: Subject to any disclaimer, the term of this patent is extended or adjusted under 35 U.S.C. 154(b) by 61 days.

(21) Appl. No.: 14/897,244

(22) PCT Filed: Apr. 16, 2014

(86) PCT No.: PCT/ZA2014/000020
§ 371 (c)(1),
(2) Date: Dec. 10, 2015

(87) PCT Pub. No.: WO2015/003192
PCT Pub. Date: Jan. 8, 2015

(65) Prior Publication Data
US 2016/0123914 A1 May 5, 2016

(30) Foreign Application Priority Data
Jul. 4, 2013 (ZA) .................................. 2013/04996

(51) Int. Cl.
| G01N 33/22 | (2006.01) |
| F42D 5/00 | (2006.01) |
| F42D 1/05 | (2006.01) |
| F42D 1/055 | (2006.01) |
| G01N 25/50 | (2006.01) |

(52) U.S. Cl.
CPC ................. *F42D 5/00* (2013.01); *F42D 1/05* (2013.01); *F42D 1/055* (2013.01); *G01N 25/50* (2013.01)

(58) Field of Classification Search
CPC . F42D 1/045; F42D 1/05; F42D 1/055; F42D 5/00
USPC ........................ 73/35.14, 35.15, 35.16, 35.17
See application file for complete search history.

(56) References Cited

U.S. PATENT DOCUMENTS

| 5,721,493 A | 2/1998 | Paxton | |
| 2013/0036931 A1* | 2/2013 | Schlenter | F42D 1/045 102/206 |

FOREIGN PATENT DOCUMENTS

| WO | 02/099356 A2 | 12/2002 |
| WO | 2005/005921 A1 | 1/2005 |

OTHER PUBLICATIONS

International Search Report for PCT/ZA2014/000020 dated Sep. 4, 2015 (3 pages).
Written Opinion for PCT/ZA2014/000020 (5 pages).

* cited by examiner

*Primary Examiner* — Benjamin Schmitt
(74) *Attorney, Agent, or Firm* — Michael Best & Friedrich LLP

(57) ABSTRACT

A signal is injected into a wired series of detonators to obtain a reflected signal which represents a validated status of the system. The reflected signal is compared to a second reflected signal, generated in a similar way, some time later; to detect factors which affect the validated status of the system.

5 Claims, 1 Drawing Sheet

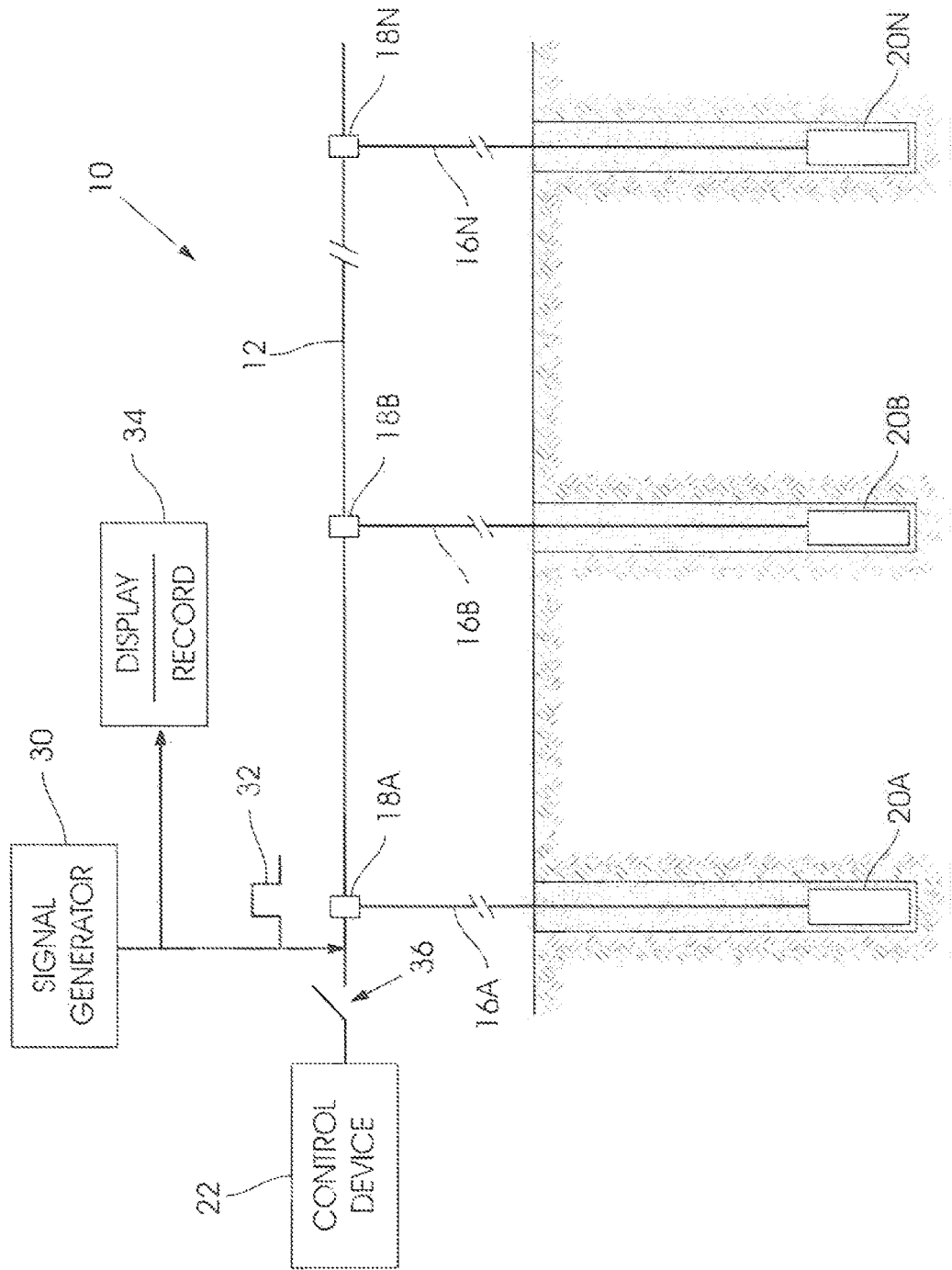

DETONATOR SYSTEM CONFIRMATION

BACKGROUND OF THE INVENTION

This invention relates generally to a wired electric or electronic detonator system and, more particularly, to a method of testing or confirming the status of this type of system.

A wired electronic detonator system may include a large number of detonators which are individually connected to a harness by means of conductive leads. The interconnection of the various components in the system can be laborious. Additionally, the integrity of the system can be compromised by various factors, environmental or manmade e.g. by the movement of machines and the like. It is thus important, before firing a detonator system, to confirm that all connections are sound and that the system is in good order.

It is, however, time consuming to implement and carry out a process to detect wire breakages or leakages in a detonator system which includes a significant umber of detonators. This type of process requires a capability to communicate directly with individual detonators in the system, in succession. Another aspect is that, during the period of time taken to carry out a conventional confirmation technique, it is quite possible that an error can occur in a part of the system which has already been tested.

It is desirable therefore to be able to test the integrity of a wired detonator system rapidly in order to reduce the likelihood of a discontinuity being present in the system, at the time the system is fired.

SUMMARY OF THE INVENTION

The invention provides a method of testing the status of a wired detonator system which includes a harness and a plurality of detonators connected to the harness, the method including the steps of:
1. from a first defined point in the system propagating a first impulse of energy into the system;
2. at a second defined point in the system recording a first observation of energy reflected by the system in response to the first impulse;
3. conducting a test on the detonator system to determine its integrity and, if the integrity of the system is validated;
4. at the first defined point propagating a second impulse of energy into the system;
5. at the second defined point recording a second observation of energy reflected by the system in response to the second impulse; and
6. comparing the first observation to the second observation to detect a variation in the integrity of the wired detonator system.

If the first observation is closely matched to the second observation then it is taken that the integrity of the detonator system, as validated by the harness test (step 3), has been confirmed. A mismatch at least in some respect, between the first observation and the second observation would be construed as indicating that a fault in the system occurred after the integrity of the system had been validated (step 3).

After a positive harness test, other work relating to the implementation of the blasting system can be carried out. Immediately before firing, and this can be at an end of an extended time interval after the harness test has been conducted the second observation is recorded and compared to the first observation (steps 4, 5 and 6). If this comparison is positive then the detonator system can be initiated.

Although it is possible for the first defined point to be displaced from the second defined point it is preferred in order to ensure that the entire detonator system traversed by the impulse, and at least for the sake of convenience, for the first defined point to be the same as the second defined point, and close to, or at, one physical end of the detonator system.

Step No. 3 can be conducted before steps 1 and 2. An intention in this respect is to have the capability of uniquely associating a waveform, produced by one or more reflections of an impulse which is injected into the detonator system, with the integrity of the detonator system.

In a broad sense therefore the invention is based on the principle that once the integrity of the wired detonator system has been confirmed, a characteristic which is associated with such confirmed integrity is determined by means of a first recordal process and, at a selected time period thereafter, a second recordal process is undertaken to determine what should be the same characteristic. If the two characteristics so determined are essentially the same then it is taken that the integrity of the system remains unaltered and firing can then take place.

BRIEF DESCRIPTION OF THE DRAWING

The invention is further described by way of example with reference to the accompanying drawing which is a block diagram representation of the manner in which the integrity of a wired electronic detonator system can be monitored in accordance with the invention.

DESCRIPTION OF PREFERRED EMBODIMENT

The accompanying drawing illustrates, in block diagram form, a wired electronic detonator system 10 which includes a wire harness 12 to which a plurality of detonators 14A, 14B . . . 14N are connected. Each detonator is coupled to the harness via a respective branch line 16A, 16B . . . 16N. Use is made of appropriate connectors 18A, 18B . . . 18N for this purpose. Each detonator is located, as is known in the art, in a respective borehole 20A . . . 20N.

The number of detonators 14 in the blasting system can be substantial e.g. several hundred. The time taken to connect each branch line 16 between the harness 12 and the corresponding detonator 14 can be considerable. Working conditions can be arduous and are influenced by environmental conditions and manmade factors such as the passage of earthmoving machines, drilling, machines, trucks with explosives and the like.

The detonator system is connected to, and is under the control of, a control device 22, such as a blasting machine. The system can be initiated by means of firing signals sent from the control device 22 after various safety protocols have been carried out. It is important to ensure that, as far as is possible, the blasting system's integrity has not been compromised in any way at the time of firing. For example, a break in one of the wires in the harness or in the branch lines, or a bad connection to a detonator, or leakage from any of the conductors, can adversely affect the blasting process. Typically before initiation takes place a full harness test is carried out to confirm that the system is sound. If a malfunction is detected then remedial action must be taken. However, the time taken to conduct a full harness test of this type can be substantial and the possibility exists that, while the test is being carried out a fault can arise in a part of the system which has already been tested. This type of fault would therefore probably not be detected. Another factor is that, in a time period between the successful completion of a full harness test and the firing of the system, a fault can occur. Again, the occurrence of this type of fault cannot normally be detected unless a full harness test is, once more, carried out.

The implementation of the method of the invention requires the use of a signal generator 30 which is capable of generating an energy impulse 32 in the form step voltage with a required energy content and with a defined duration, a display device 34 and, optionally, an isolating switch 36.

The display device 34 may be of any appropriate kind and for example may comprise an oscilloscope or a digital signal recorder which can be used to display and record a waveform.

If the signal generator produces a signal, i.e. the energy impulse 32, which is quite different from signals used for normal detonator communication then the switch 36 is not required. If there is any degree of similarity between the energy impulse 32 and any at the normally used signals then the switch 36 would be used. In any event, from a safety point of view, it is desirable to use the switch.

The control device 22 is isolated from the blasting system by opening the switch 36. If the control device 22 is connected to the harness during impulse generation then the output impedance the device 22 must be constant.

The impulse 32 is injected into the system, via the harness, downstream of the switch 36. The impulse traverses the system and, at each electrical discontinuity or impedance change in the system, a reflection of the impulse takes place. The nature of each reflection is dependent on the nature of the discontinuity or impedance change. The various reflections travel in the reverse direction along the detonator system and produce a compound waveform which is dependent, in a unique manner, on the prevailing characteristics, including discontinuities, in the blasting system.

Data on the compound reflected waveform, resulting from the first injection of the impulse into the system, is recorded. Subsequently a full harness test is done on the detonator system using appropriate techniques. For example, each detonator is interrogated and tested on an individual basis. If the integrity of the detonator system is confirmed by the full harness test then the compound reflected waveform is taken to represent a condition in which the integrity of the detonator system has not been compromised.

If the harness test confirms the integrity of the detonator system then further implementation of the blasting process may be carried out as appropriate. However, if the harness test reveals one or more faults in the system appropriate remedial steps are taken to correct the faults.

After all further work relating to the implementation of the blasting system has been carried out, but before firing is to take place, a second energy impulse, identical to the energy impulse which is associated with the blasting system of confirmed integrity, is injected into the system with the switch 32 open (as the case may be). The injection is done at the location at which the first impulse was injected into the system. A compound reflected waveform which is determined by the characteristics, including discontinuities, of the detonator system, is detected, displayed, and recorded, by the instrument 34. If the second reflected waveform is substantially identical to the first reflected waveform then it is taken that the integrity of the blasting system has not been compromised in the intervening time period. Firing can then take place. If there are significant differences e.g. on an amplitude or time basis, between the second reflected waveform and the first reflected waveform, then this is indicative that a fault has occurred in the detonator system and suitable testing sequences are carried out to identify the fault so that corrective action can be taken.

In carrying out the method of the invention it is possible to compare a full reflected waveform directly to another full reflected waveform. Alternatively, essential characteristics of each reflected waveform, such as maximum amplitude, number of amplitude peaks, and duration of the waveform, are recorded. This may be done using digital techniques. The sets of characteristics are then compared to one another instead of comparing the complete or full waveforms to each other.

A unique compound reflected signal can be recorded at any stage while the blasting system is being established.

A significant benefit of the invention lies in the fact that the generation of the injected impulses, the reception and storage of each resulting reflected waveform, and the comparison process referred to, are done rapidly. This means that it is possible to validate the integrity of the detonator system at any stage while it is being established. In particular, though, the integrity of the system can be rapidly validated immediately before firing takes place with a high degree of certainty that the detonator system will be sound at the time of firing.

The invention claimed is:

1. A method of testing the status of a wired detonator system which includes a harness and a plurality of detonators connected to the harness, the method including the steps of:
   1) from a first defined point in the system propagating a first impulse of energy into the system;
   2) at a second defined point in the system recording a first observation of energy reflected by the system in response to the first impulse;
   3) conducting a test on the detonator system to determine its integrity and, if the integrity of the system is validated;
   4) at the first defined point propagating a second impulse of energy into the system;
   5) at the second defined point recording a second observation of energy reflected by the system in response to the second impulse; and
   6) comparing the first observation to the second observation to detect a variation in the integrity of the wired detonator system.

2. The method according to claim 1 wherein, if the first observation is substantially similar to the second observation, then the integrity of the detonator system, as validated by the harness test (step 3), is confirmed.

3. The method according to claim 1 wherein the first defined point is the same as the second defined point.

4. The method according to claim 1 wherein step 3 is before steps 1 and 2, and wherein steps 4, 5 and 6 are conducted a period of time after steps 1 and 2.

5. The method according to claim 1 wherein, to carry out step 6, respective sets of characteristics of each observation are compared.

* * * * *